(12) United States Patent
Mittauer et al.

(10) Patent No.: US 10,471,278 B2
(45) Date of Patent: Nov. 12, 2019

(54) CRANIAL ALIGNMENT DEVICE FOR USE IN INTRACRANIAL STEREOTACTIC SURGERY

(71) Applicant: University of Florida Research Foundation, Incorporated, Gainesville, FL (US)

(72) Inventors: Kathryn Elizabeth Mittauer, Ocala, FL (US); Guanghua Yan, Gainesville, FL (US); Richard Helmig, Hawthorne, FL (US); Chihray Liu, Gainesville, FL (US); Bo Lu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 495 days.

(21) Appl. No.: 14/316,396

(22) Filed: Jun. 26, 2014

(65) Prior Publication Data
US 2015/0374443 A1    Dec. 31, 2015

(51) Int. Cl.
*A61N 5/10* (2006.01)
*A61B 90/00* (2016.01)
(Continued)

(52) U.S. Cl.
CPC ............ *A61N 5/1049* (2013.01); *A61B 90/18* (2016.02); *A61B 90/39* (2016.02); *A61F 9/04* (2013.01);
(Continued)

(58) Field of Classification Search
CPC .. A61N 5/1084; A61N 5/1049; A61N 5/1051; A61N 5/1077; A61N 5/10; A61N 5/1048; A61N 2005/105–1063; A61N 2005/1092; A61N 2005/1097; A61F 9/00; A61F 9/02; A61F 9/026; A61F 9/04–068; A61F 2210/00; A61F 2210/0071; A61F 2240/00; A61F 2240/001–004; A61F 2250/00; A61F 2250/0058; A61F 2250/0096; A61B 90/18; A61B 90/39; A61B 90/14; A61B 90/36; A61B 2090/363; A61B 2090/392; A61B 2090/3904–3995; A61B 34/20; A61B 90/00; A61B 90/10; A61B 2090/101; A61B 2034/2046; A61B 2034/2055; G02C 5/12–128; G02C 5/00;
(Continued)

(56) References Cited

U.S. PATENT DOCUMENTS 3,233,250 A * 2/1966 Severin .................. A61F 9/025
2/443
3,594,813 A * 7/1971 Sanderson ............ A61F 13/126
128/857
(Continued)

OTHER PUBLICATIONS

International Search Report dated Sep. 30, 2015 for PCT/US15/37366 filed Jun. 24, 2015.
(Continued)

*Primary Examiner* — Victoria J Hicks
*Assistant Examiner* — Michelle J Lee
(74) *Attorney, Agent, or Firm* — Timothy H. Van Dyke; Beusse, Wolter, Sanks & Maire PLLC

(57) ABSTRACT

A cranial alignment device for use in intracranial stereotactic radiotherapy includes a nosepiece that is custom shaped to mate with the dorsum and alae of the patient's nose.

15 Claims, 4 Drawing Sheets

(51) Int. Cl.
  *A61B 90/18* (2016.01)
  *A61F 9/04* (2006.01)
  *A61B 34/20* (2016.01)
  *A61B 90/10* (2016.01)

(52) U.S. Cl.
  CPC .... *A61N 5/1084* (2013.01); *A61B 2034/2055* (2016.02); *A61B 2090/101* (2016.02); *A61B 2090/397* (2016.02); *A61B 2090/3979* (2016.02); *A61B 2090/3983* (2016.02); *A61F 2210/0071* (2013.01); *A61F 2240/001* (2013.01); *A61F 2250/0096* (2013.01); *A61N 2005/1059* (2013.01); *A61N 2005/1097* (2013.01)

(58) Field of Classification Search
  CPC .... G02C 5/02–10; A41D 13/00; A41D 13/05; A41D 13/11–1192
  USPC ...................... 351/131, 132; 2/446
  See application file for complete search history.

(56) References Cited

U.S. PATENT DOCUMENTS

| | | | | |
|---|---|---|---|---|
| 3,597,053 | A * | 8/1971 | Mastman | G02C 5/122 264/222 |
| 4,704,015 | A * | 11/1987 | Grendol | G02C 5/126 351/137 |
| 4,868,930 | A * | 9/1989 | Blackstone | A61F 9/02 2/439 |
| 4,945,914 | A * | 8/1990 | Allen | A61B 6/12 600/426 |
| 6,122,541 | A | 9/2000 | Cosman et al. | |
| 6,132,437 | A | 10/2000 | Omurtag | |
| 6,175,756 | B1 | 1/2001 | Ferre et al. | |
| 6,640,127 | B1 * | 10/2003 | Kosaka | A61B 90/36 600/414 |
| 7,231,723 | B1 | 6/2007 | O'Neill | |
| 7,925,328 | B2 | 4/2011 | Urquhart et al. | |
| 8,457,719 | B2 | 6/2013 | de la Barrera et al. | |
| 2004/0064890 | A1 | 4/2004 | Kim | |
| 2005/0054910 | A1 * | 3/2005 | Tremblay | A61B 5/055 600/411 |
| 2005/0075560 | A1 * | 4/2005 | Hannula | A61B 90/39 600/424 |
| 2006/0005839 | A1 * | 1/2006 | Woodburn | A61B 6/0421 128/206.29 |
| 2008/0006274 | A1 | 1/2008 | Thornton | |
| 2008/0075560 | A1 | 3/2008 | Kurabayashi et al. | |
| 2014/0186793 | A1 * | 7/2014 | Kurti, Jr. | A61B 5/742 433/73 |
| 2014/0366889 | A1 * | 12/2014 | Riley | A61F 9/045 128/845 |

OTHER PUBLICATIONS

Written Opinion dated Sep. 30, 2015 for PCT/US15/37366 filed Jun. 24, 2015.

* cited by examiner

CRANIAL ALIGNMENT DEVICE FOR USE IN INTRACRANIAL STEREOTACTIC SURGERY

BACKGROUND OF THE INVENTION

The invention relates to radiotherapy, and more particularly relates to stereotactic radiotherapy. In its most immediate sense, the invention relates to intracranial stereotactic radiotherapy.

In radiotherapy, a treatment beam of high-energy radiation is made incident on to a tumor that is to be destroyed. In intracranial stereotactic radiotherapy, an image-guided radiotherapy apparatus ("IGRT" apparatus) is used to destroy a brain tumor. An IGRT apparatus includes an imaging system such as a cone-beam computed tomography system (a "CBCT" system) and a linear accelerator. The imaging system is used to acquire an image of the tumor and the linear accelerator is used to produce the treatment beam, which is aimed at the tumor to destroy it.

In order to carry out intracranial stereotactic radiotherapy successfully, two localizations must occur. One of these localizations is carried out by the imaging modality; the e.g. CBCT image localizes the tumor within the patient's head. The other required localization is the localization of the patient's head within the coordinate system of the IGRT apparatus. This is carried out using an alignment device that is recognized by the IGRT apparatus or by equipment that is used together with it.

Before the patient's treatment begins, the alignment device is mounted to the patient and a computed tomography study (a "simulation") is carried out to acquire an image of the patient's head. During this image acquisition, the alignment device is used to register the precise location and orientation of the patient's head. Then, the information acquired during this simulation is used to develop a treatment plan for irradiating the tumor. To treat a patient who has been placed within the IGRT apparatus, the alignment device is used again to localize the patient's actual head position within the coordinate system of the IGRT apparatus and to place the patient's head in a location that precisely matches the position and orientation of the patient's head during the simulation procedure. And, since the position of the tumor within the patient's head is known from the image acquired during simulation, the treatment plan can be executed to destroy the tumor with little or no destruction of healthy tissue that surrounds the tumor.

The alignment device must operate with a high degree of repeatability because the localization of the patient within the IGRT apparatus must always be precise. If the alignment device works differently during patient imaging then during patient treatment, or if it works differently during successive treatments, the beam of ionizing radiation will be inaccurately aimed. This will cause unnecessary destruction of healthy tissue and insufficient destruction of tumor tissue.

In one category of alignment devices, a component with a known structure is physically attached to the patient's head and interacts with apparatus that registers the location of the component. This permits the location of the patient's head to be accurately determined. For example, the SonArray device manufactured by Varian has a bite plate that is held in the patient's mouth. Proper repeat positioning of the patient using the SonArray device requires the patient to bite with consistent pressure. This can be difficult. In addition, the SonArray device can be uncomfortable in use, especially with patients who have had teeth extracted (as is the case with many head and neck radiotherapy patients). Furthermore, if the patient swallows his or her saliva, the SonArray device can move with respect to the patient, causing the position of patient's head to be mis-registered within the coordinate system of the IGRT apparatus.

In the AlignRT device manufactured by Vision RT, the position of the patient is determined by image processing. The AlignRT device acquires images of the patient's head using two cameras whose locations and orientations are precisely known. After the two images are acquired, the device identifies patient features that appear in both images and then reconstructs 3D surface data to localize the patient's head using triangulation. If the patient loses weight or the pattern of the patient's facial hair changes (both conditions are often encountered with chemotherapy), the precision with which the patient's head is localized can be adversely affected.

It would be advantageous to provide a cranial alignment device for use in intracranial stereotactic radiotherapy that is comfortable, that does not require effort from the patient, and that operates with a high degree of repeatability even if the patient loses or gains weight, and even if the patient's hair pattern changes (hair loss occurs in patients who undergo chemotherapy).

One object of the invention is to provide a method for reproducibly positioning a patient's head, and a cranial alignment device for use in intracranial stereotactic radiotherapy, that are comfortable for the patient, that do not require the patient to exert effort, and that operate with a high degree of repeatability even if the patient's surface anatomy changes (as by gain or loss of weight or hair loss).

Another object is, in general, to improve on known devices and methods of this general type.

The invention proceeds from the realization that for any patient, the shapes of the dorsum and alae of the patient's nose do not change when the patient gains or loses weight. Furthermore, these locations seldom have substantial hair growth. Thus, an alignment device that is mounted to the patient's head using a custom shaped nosepiece that mates with the dorsum and alae of the patient's nose will always fit on the patient's head in precisely the same way and in a rigid manner. This will be true whether the patient gains or loses weight or whether the patient loses hair.

A device in accordance with the invention has two earpieces and a front frame that is connected between them. These components are dimensioned to fit upon a patient's face with the front frame in front of the patient's eyes and each earpiece engaging behind one of the patient's ears. The device further has a nosepiece that is custom shaped to mate with the dorsum and alae of the patient's nose and that is detachably securable to the front frame. The device also has a plurality of infrared-reflecting markers mounted on the front frame.

A device in accordance with the invention is worn on the patient's head like a pair of eyeglasses. The patient is not required to exert any effort to keep the device in place, and changes in the patient's weight and hair patterns do not affect the way the device fits on the patient's head. A conventional optical tracking system such as is conventionally used with IGRT apparatus can be used to register with six-degrees-of-freedom (translation and rotation) the position of the device—and therefore the position of the patient's head—in the coordinate system of the IGRT apparatus.

A device in accordance with the invention is inexpensive and simple to make and to fit to a patient. And, no additional equipment is needed because an optical tracking system will likely be available anyway.

Advantageously, the infrared-reflecting markers are not coplanar and are positioned asymmetrically in two groups, each group being associated with one of the patient's eyes. Such a pattern minimizes the likelihood that the optical tracking system will improperly localize the device within the coordinate system of the IGRT apparatus.

In a method in accordance with the invention, a nosepiece that mates with the dorsum and alae of the patient's nose is created. The nosepiece is attached to a fixture that is adapted for mounting on the patient's head, and the fixture is mounted on the patient's head.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

The drawings are not necessarily to scale, and individual parts may be enlarged or reduced for clarity.

Figure 1:
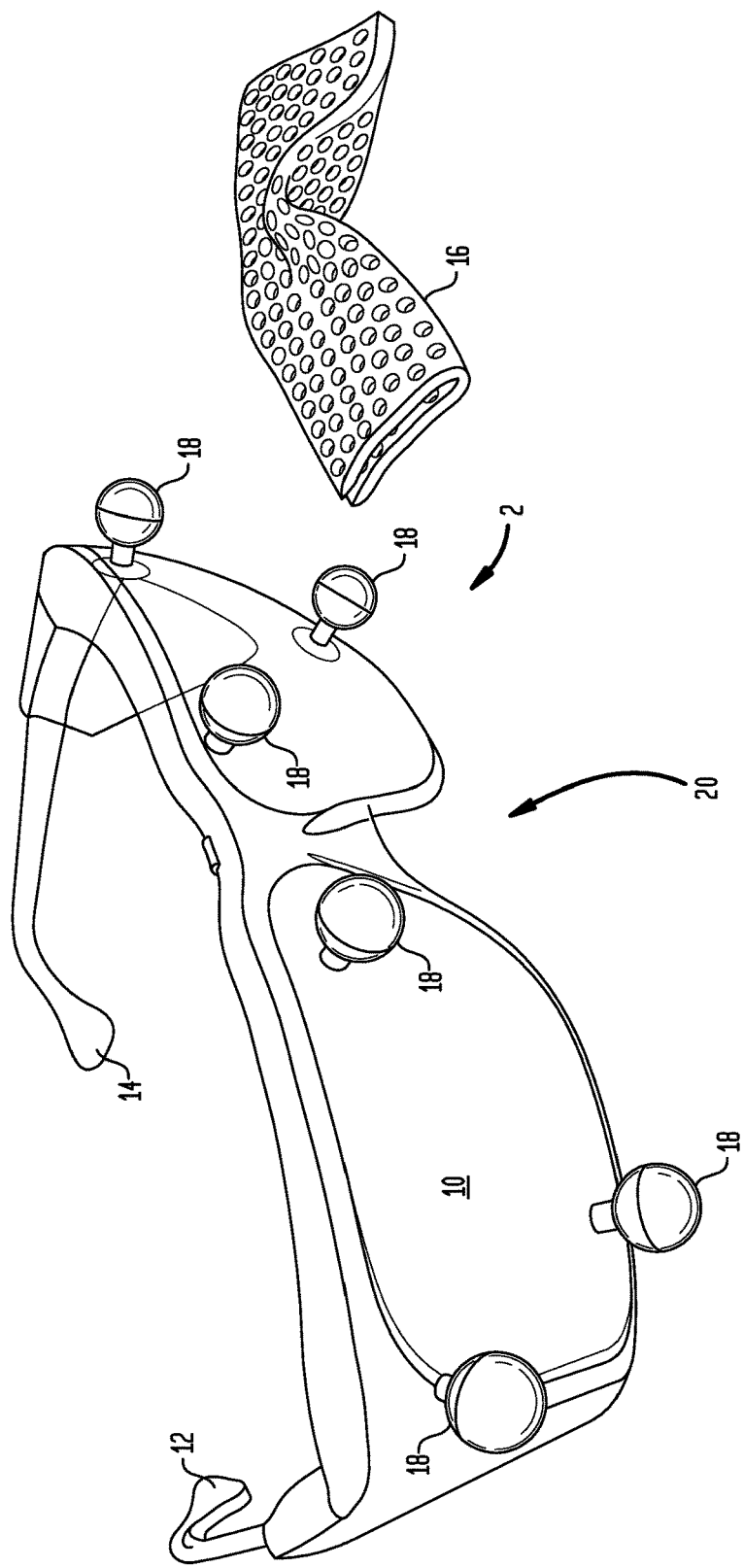
FIG. 1 shows a preferred embodiment of a device in accordance with the invention before assembly.
Figure 3:
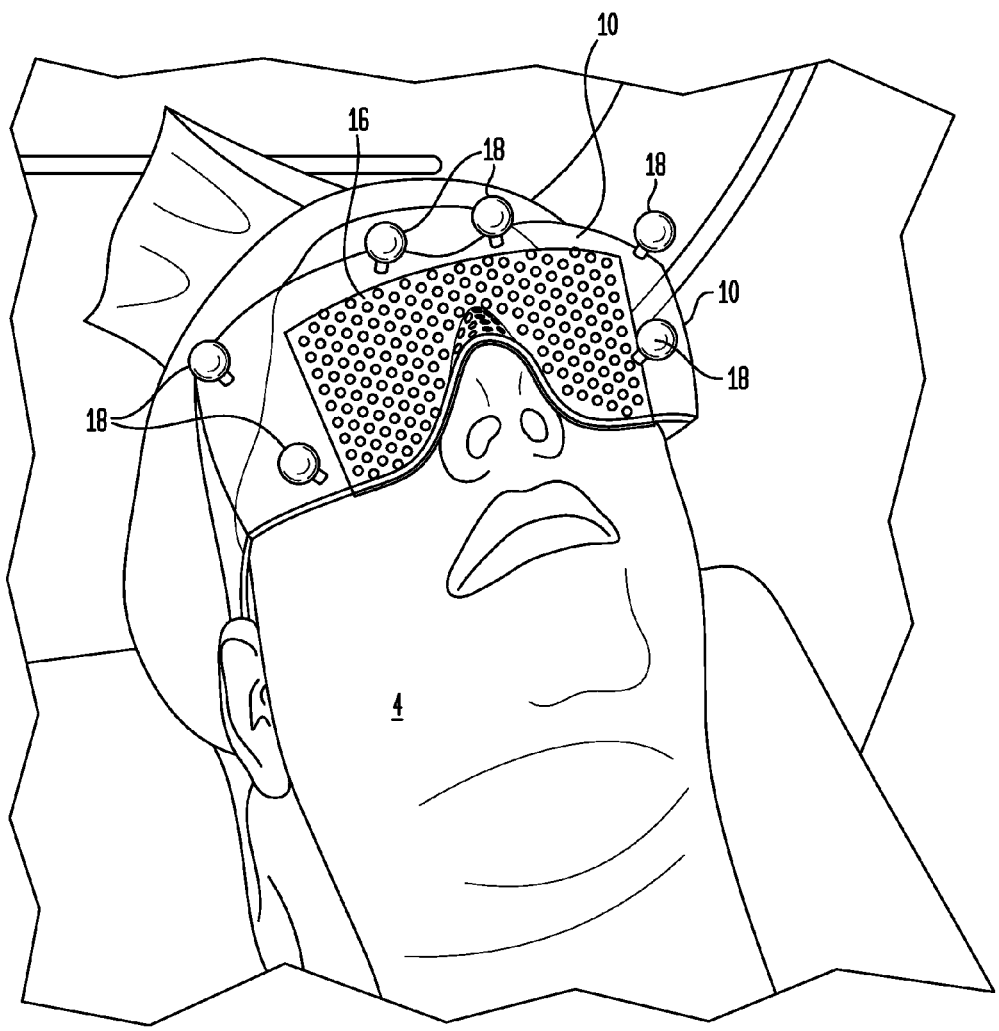
FIG. 3 illustrates a preferred embodiment of a device in accordance with the invention mounted on a patient.
Figure 4:
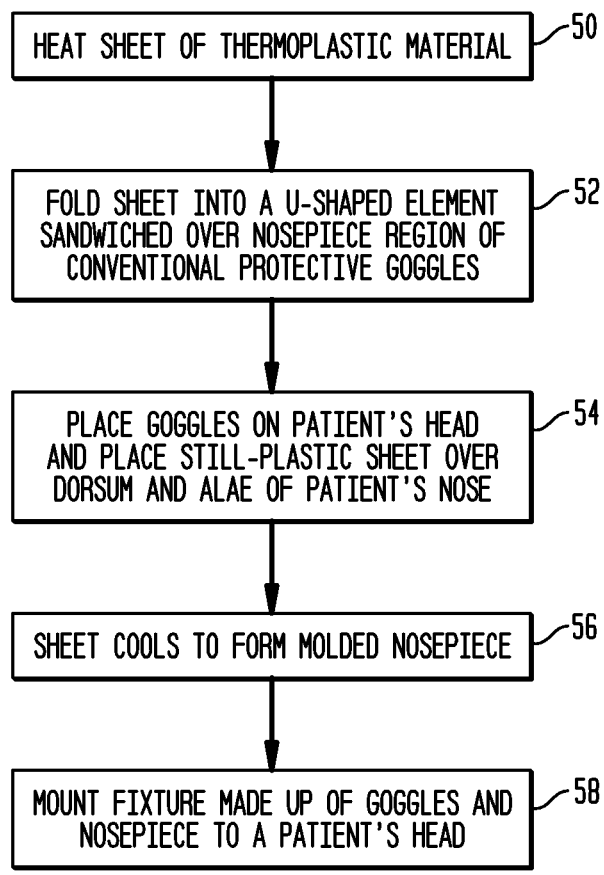
FIG. 4 is a flow chart of a preferred embodiment of a method in accordance with the invention.

Referring first to FIG. 1, a cranial alignment device for use in intracranial stereotactic radiotherapy generally indicated by reference numeral 2 has a front frame 10 connected between two earpieces 12 and 14. The front frame 10 and the earpieces 12 and 14 are dimensioned to fit upon the face of a patient 4 (FIG. 3) with the front frame in front of the eyes of the patient 4 and with each earpiece engaging behind one of the ears of the patient 4 (see FIG. 3). Advantageously, the front frame 10 and earpieces 14 are parts of a conventional pair of protective goggles.

Figure 2:
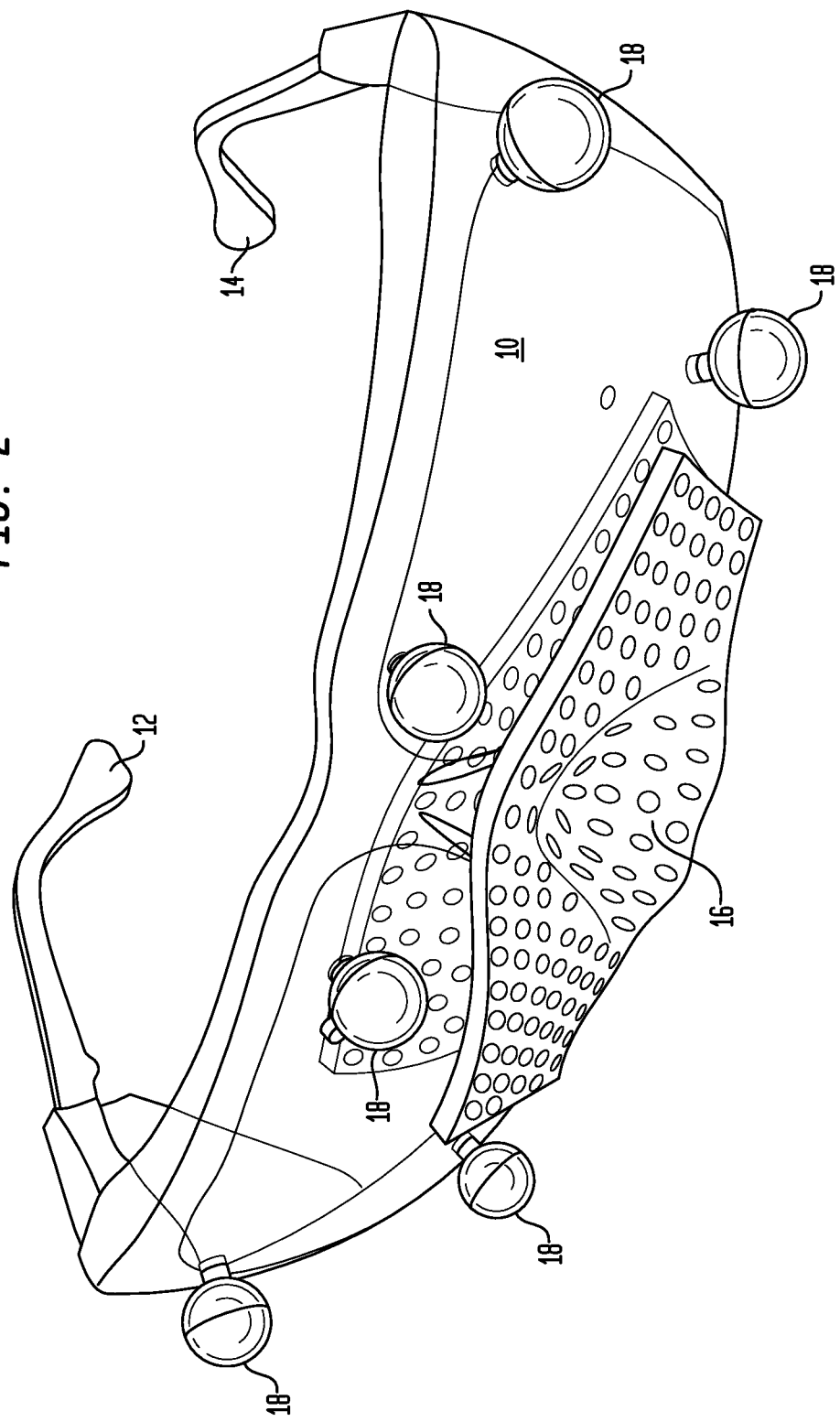
FIG. 2 shows a preferred embodiment of a device in accordance with the invention in the assembled state.

A nosepiece 16 is formed from a sheet of thermoplastic. (Advantageously but not necessarily, the thermoplastic is available in sheet form from Klarity Medical as product number R-3242A.) The sheet is placed in hot water until it is appropriately pliable. Once the sheet has been withdrawn from the hot water, the sheet is folded into a U that encloses the nosepiece region 20 of the front frame 10. Then, the front frame 10 and earpieces 12 and 14 are placed on the patient's face, and the sheet is pressed over the dorsum and the two alae of a patient's nose. In this way, the sheet is made to conform to the patient 4 and to the nosepiece region 20 of the front frame 10 in a single operation. (The sheet may also be—and in the preferred embodiment is—pressed over the radix of the patient's nose and onto the patient's forehead, but this is not required.) The sheet, after cooling, becomes rigid and forms the nosepiece 16. When the nosepiece region 20 of the front frame 10 has been slipped into the U of the nosepiece 16 as shown in FIG. 2 the device 2 fits securely on the head of the patient 4 in a consistently repeatable manner (see FIG. 3).

Six infrared-reflective markers 18 are mounted to the front frame 10 at locations that are known precisely. Such markers are used because an optical tracking system (not shown) of the type conventionally used with an IGRT apparatus uses such markers as fiducials. The markers 18 are not coplanar, no three of them are collinear, and they are positioned asymmetrically in two groups, each group being associated with one of the patient's eyes (see FIG. 3). This minimizes the likelihood that the optical tracking system will improperly localize the device 2.

In the initial step 50 of a method in accordance with a preferred embodiment of the invention, a sheet of thermoplastic material is heated so as to become plastic. In the next step 52, the sheet is folded into a U-shaped element that is sandwiched over the nosepiece region of a conventional pair of protective goggles. Subsequently, in step 54, the goggles are placed on the patient's head and the still-plastic sheet is placed over the dorsum and alae of the nose of a patient who is to undergo intracranial stereotactic radiotherapy. When the sheet cools (step 56), a nosepiece is formed; the nosepiece mates with the dorsum and alae of the patient's nose as well as with the nosepiece region of the protective goggles. This enables the resulting fixture made up of the goggles and the nosepiece to be mounted to a patient's head (step 58) in a highly repeatable manner.

Although a preferred embodiment has been described above, the scope of the invention is determined only by the following claims:

The invention claimed is:

1. A cranial alignment device for use in intracranial stereotactic radiotherapy, the device comprising:
    two earpieces;
    a front frame between and connecting the two earpieces, the front frame configured and adapted for fitting in front of a first eye and a second eye on a face of a patient receiving intracranial stereotactic radiotherapy and each of the two earpieces configured and adapted to engage an ear of the patient;
    a nosepiece comprising a sheet of thermoplastic material that is folded over onto itself to form a U-shaped element comprising a bend between two folds, wherein the two folds are sandwiched over a nosepiece-receiving region of the front frame, wherein the bend is disposed apart from the front frame, wherein the bend defines a perimeter of a concave pocket in the nosepiece that protrudes from the front frame and which is adapted to drape over and conform to a dorsum and alae of a nose of the patient, wherein in the pocket a second fold of the two folds is adapted to rest directly on the dorsum and the alae and comprises a shape that is adapted to mate with the dorsum and the alae, and a first fold of the two folds rests atop the second fold, is adapted to rest over the dorsum and the alae, and comprises a shape that mates with the second fold; and
    a plurality of infrared-reflecting markers mounted to the front frame and comprising a first group and a second group of markers, the first group arranged on a first lens-shaped piece of the front frame and configured to locate the first eye of the patient and the second group arranged on a second lens-shaped piece of the front frame and configured to locate the second eye of the patient,
    wherein the cranial alignment device is free of infrared-reflecting markers other than the plurality of infrared-reflecting markers mounted to the first lens-shaped piece and the second lens-shaped piece.

2. The device according to claim 1, wherein the plurality of infrared-reflecting markers comprises three markers in each of the first group and the second group of markers, wherein the three markers in each of the first group and the second group are positioned and arranged such that an optical tracking system is configured to properly locate the device.

3. The device according to claim 1, wherein there is no symmetry about the nosepiece-receiving region between infrared-reflecting markers in the first group and infrared-reflecting markers in the second group.

4. The device according to claim 1, wherein infrared-reflecting markers in the first group define a first plane, infrared-reflecting markers in the second group define a second plane, and the first plane and the second plane are not coplanar.

5. The device according to claim 1, wherein the sheet of thermoplastic material is further shaped and adapted to conform with a shape of a radix of the nose of the patient and to a forehead of the patient when the sheet of thermoplastic material becomes rigid.

6. The cranial alignment device of claim 1, wherein the sheet of thermoplastic material comprises a uniform thickness.

7. The cranial alignment device of claim 1, wherein the sheet of thermoplastic material comprises a sheet of splinting material.

8. A method for preparing a device for reproducibly positioning a head of a patient, the method comprising steps of:
rendering a single sheet of thermoplastic pliable into a pliable sheet of thermoplastic;
folding the pliable sheet of thermoplastic into a U-shaped element comprising a bend between pliable folds, wherein the folds sandwich a nosepiece region, a first lens-shaped piece, and a second lens-shaped piece of a cranial alignment device therebetween;
molding the pliable sheet of thermoplastic to conform the pliable sheet of thermoplastic to a shape of a dorsum and alae of a nose of the patient and also to a shape of the nosepiece region, the first lens-shaped piece, and the second lens-shaped piece;
molding the pliable sheet of thermoplastic to form a pocket that protrudes from between the first lens-shaped piece and the second lens-shaped piece and which is adapted to drape over and conform to the dorsum and the alae, wherein in the pocket a second fold of the folds is adapted to rest on the dorsum and the alae and comprises a shape that mates with the dorsum and the alae, and a first fold of the folds rests atop the second fold, rests over the dorsum and the alae, and comprises a shape that mates with the second fold, wherein the bend crosses a gap between the first lens-shaped piece and the second lens-shaped piece and is disposed apart from the first lens-shaped piece and from the second lens-shaped piece, and wherein the bend defines a perimeter of the pocket,
cooling the pliable sheet of thermoplastic to form a rigid nosepiece comprising a new shape that conforms to the shape of the dorsum and the alae of the nose of the patient and also to the shape of the nosepiece region, the first lens-shaped piece, and the second lens-shaped piece; and
arranging a plurality of infrared-reflecting markers in a first group and a second group, the first group arranged on the first lens-shaped piece and the second group arranged on the second lens-shaped piece.

9. The method according to claim 8, further comprising positioning the device at a predetermined location.

10. The method according to claim 8, wherein molding the pliable sheet of thermoplastic further comprises molding the pliable sheet to conform to a shape of a radix of the nose of the patient and to a forehead of the patient.

11. The cranial alignment device for use in intracranial stereotactic radiotherapy prepared according to the method of claim 8.

12. A cranial alignment device, comprising:
two earpieces, a first lens-shaped piece comprising a first group of infrared-reflecting markers disposed thereon, a second lens-shaped piece comprising a second group of infrared-reflecting markers disposed thereon, a gap between the first lens-shaped piece and the second lens-shaped piece, a nosepiece region between the first group and the second group, and a nosepiece,
wherein the nosepiece comprises a single sheet of thermoplastic material that is folded over onto itself to form a bend between a first fold and a second fold, wherein the first fold and the second fold sandwich therebetween the nosepiece region, the first lens-shaped piece, and the second lens-shaped piece,
wherein the first fold conforms to a front of the nosepiece region, a front of the first lens-shaped piece, and a front of the second lens-shaped piece, wherein the second fold conforms to a rear of the nosepiece region, a rear of the first lens-shaped piece, and a rear of the second lens-shaped piece,
wherein the bend crosses the gap and is disposed apart from the first lens-shaped piece, apart from the second lens-shaped piece, and apart from the nosepiece region, wherein the bend defines a perimeter of a pocket in the nosepiece that protrudes from between the first lens-shaped piece and the second lens-shaped piece and which is adapted to drape over and conform to a dorsum and alae of a patient, wherein in the pocket: the second fold comprises a first side adapted to rest on the dorsum and the alae and a second side opposite the first side, the second fold comprises a shape that is adapted to mate with the dorsum and the alae, the first fold is adapted to rest over the dorsum and the alae, a first side of the first fold rests atop the second side of the second fold, and the first side of the first fold comprises a shape that mates with a shape of the second side of the second fold,
wherein a resilience of the nosepiece resists separation of the folds, thereby retaining the nosepiece in place, and wherein the nosepiece is sufficiently elastically flexible to permit the folds to be separated under force, thereby releasing the nosepiece.

13. The cranial alignment device of claim 12, wherein the cranial alignment device is free of infrared-reflecting markers other than the first group of infrared-reflecting markers and the second group of infrared-reflecting markers.

14. The cranial alignment device of claim 12, wherein the single sheet of thermoplastic material comprises a uniform thickness.

15. The cranial alignment device of claim 12, wherein the single sheet of thermoplastic material comprises a sheet of splinting material.

* * * * *